United States Patent
Collins et al.

(10) Patent No.: US 12,421,184 B2
(45) Date of Patent: Sep. 23, 2025

(54) PROCESSES FOR THE PYROLYSIS OF CARBOHYDRATES

(71) Applicant: Archer Daniels Midland Company, Decatur, IL (US)

(72) Inventors: William J. Collins, Mt. Zion, IL (US); Josh Terrian, Mt. Zion, IL (US); James Brazdil, Leland, NC (US); Kevin Martin, Mt. Zion, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 0 days.

(21) Appl. No.: 17/998,344

(22) PCT Filed: Apr. 28, 2021

(86) PCT No.: PCT/US2021/029660
§ 371 (c)(1),
(2) Date: Nov. 9, 2022

(87) PCT Pub. No.: WO2021/231089
PCT Pub. Date: Nov. 18, 2021

(65) Prior Publication Data
US 2023/0227391 A1     Jul. 20, 2023

Related U.S. Application Data

(60) Provisional application No. 63/023,763, filed on May 12, 2020.

(51) Int. Cl.
| | |
|---|---|
| C07C 45/60 | (2006.01) |
| B01J 21/08 | (2006.01) |
| B01J 23/28 | (2006.01) |
| B01J 23/30 | (2006.01) |
| B01J 35/30 | (2024.01) |
| B01J 35/61 | (2024.01) |
| B01J 37/02 | (2006.01) |
| B01J 37/03 | (2006.01) |

(52) U.S. Cl.
CPC ............... *C07C 45/60* (2013.01); *B01J 21/08* (2013.01); *B01J 23/28* (2013.01); *B01J 23/30* (2013.01); *B01J 35/394* (2024.01); *B01J 35/612* (2024.01); *B01J 35/613* (2024.01); *B01J 35/615* (2024.01); *B01J 35/617* (2024.01); *B01J 37/0219* (2013.01); *B01J 37/0221* (2013.01); *B01J 37/035* (2013.01)

(58) Field of Classification Search
CPC ...................................................... C07C 45/60
See application file for complete search history.

(56) References Cited

U.S. PATENT DOCUMENTS

| | | |
|---|---|---|
| 5,252,188 A | 10/1993 | Stradal et al. |
| 7,094,932 B2 | 8/2006 | Majerski et al. |
| 2004/0022912 A1 | 2/2004 | Majerski et al. |
| 2015/0307786 A1 | 10/2015 | Dayton et al. |
| 2017/0197893 A1 | 7/2017 | Mårup Osmundsen et al. |
| 2018/0142159 A1 | 5/2018 | Kumar et al. |

FOREIGN PATENT DOCUMENTS

| | | |
|---|---|---|
| CN | 109790098 A | 5/2019 |
| EP | 0423393 A1 | 4/1991 |
| JP | H06506361 A | 7/1994 |
| JP | 2015516474 A | 6/2015 |
| JP | 2019518011 A | 6/2019 |
| JP | 2019536808 A | 12/2019 |
| WO | 2018104508 | 6/2018 |
| WO | 2021032590 A1 | 2/2021 |

OTHER PUBLICATIONS

Osmundsen, C.M., "Catalytic Conversion of Carbohydrates", Welcome to DTU Research Database Logo, Department of Physics, Technical University of Denmark, pp. 1-123 (Feb. 1, 2013).

*Primary Examiner* — Golam M Shameem
(74) *Attorney, Agent, or Firm* — Jesse S. Harper

(57) ABSTRACT

Various processes for the pyrolysis of carbohydrates to prepare products such as glycolaldehyde are described. Also, various catalysts and processes for preparing catalysts useful for carbohydrate pyrolysis are described.

20 Claims, No Drawings

PROCESSES FOR THE PYROLYSIS OF CARBOHYDRATES

CROSS-REFERENCE TO RELATED APPLICATIONS

This application is a national stage entry of International Application No. PCT/US21/29660, filed Apr. 28, 2021, which itself claims priority to U.S. Provisional Patent Application No. 63/023,763, filed May 12, 2020, the contents of each are incorporated herein by reference.

FIELD OF THE INVENTION

The present invention relates to various processes for the pyrolysis of carbohydrates to prepare products such as glycolaldehyde (also known as hydroxyacetaldehyde). The present invention further relates to various catalysts and processes for preparing catalysts useful for carbohydrate pyrolysis.

BACKGROUND

For many years, there has been an interest in using biomass feedstocks rich in carbohydrates to produce commercially useful chemicals. Pyrolysis of biomass feedstocks is a potentially attractive process to produce a range of chemical products and intermediates such as glycolaldehyde, methylglyoxal/pyruvaldehyde, acetol/hydroxyacetone, and formaldehyde. Of these chemicals, glycolaldehyde is a particularly versatile chemical for a range of valuable and strategic products in the nutrition and renewable materials industries. For example, glycolaldehyde is useful as a browning agent and flavoring in food applications (e.g., liquid smoke). Also, this compound can be used as a building block for various amines, polyols, sugars, and sugar alcohols.

The biomass feedstocks (e.g., cellulose/glucose-containing feedstocks), reaction medium (e.g., sand), carrier gases (e.g., nitrogen), and materials of constructions used in typical processes and apparatus for the pyrolysis of biomass are relatively inexpensive. However, pyrolysis of these feedstocks is also an inherently energy intensive process, typically requiring constant heating at temperatures in excess of 500° C. and additional means to facilitate heat transfer. Also, yields of desired products including glycolaldehyde have been limited in prior attempts. For example, U.S. Pat. No. 7,094,932 reports glycolaldehyde yields ranging from 55% to 70%. Further, some pyrolysis processes produce problematic byproducts that are difficult to separate and require special handling and disposal. The pyrolysis process also typically produces char as a byproduct. The yield of desirable products is limited by the production of char, and the char can cause operational difficulties resulting in reactor shutdown and/or lost production. Thus, there remains a need for carbohydrate pyrolysis processes that have lower operating costs, produce greater yields of desirable products such as glycolaldehyde, and/or produce decreased amounts of byproducts and/or char.

BRIEF SUMMARY

Various aspects of the present invention are directed to processes for preparing glycolaldehyde. Typically, the processes comprise feeding a feed composition comprising a carbohydrate having at least four carbon atoms to a pyrolysis reaction zone; and pyrolyzing the carbohydrate in the presence of water and a catalyst in the pyrolysis reaction zone to form a reaction product comprising glycolaldehyde, wherein the catalyst comprises a metal oxide on a catalyst support.

In some embodiments, the processes further comprise at least one of the following conditions:
(a) the pyrolysis reaction zone is heated to a temperature of about 400° C. or greater;
(b) the catalyst support has a BET specific surface area that is about 500 $m^2/g$ or less, about 250 $m^2/g$ or less, about 100 $m^2/g$ or less, about 50 $m^2/g$ or less, about 25 $m^2/g$ or less, about 10 $m^2/g$ or less, about 5 $m^2/g$ or less, or about 1 $m^2/g$ or less;
(c) the catalyst support comprises a glass, ceramic, or refractory material;
(d) the pyrolysis reaction zone further comprises a reaction zone media that is different than the catalyst; and/or
(e) the yield of glycolaldehyde is about 70% or greater, about 75% or greater, or about 80% or greater.

Additional aspects of the present invention are directed to processes for preparing catalysts useful for carbohydrate pyrolysis. In some embodiments, processes for preparing a catalyst comprise: mixing a metal oxide, a solvent, and a strong acid to form a sol-gel; depositing the sol-gel on a catalyst support to form a coated catalyst support; and removing solvent from the coated catalyst support to form the catalyst.

Further aspects of the present invention are directed to catalysts prepared by these processes.

Other objects and features will be in part apparent and in part pointed out hereinafter.

DETAILED DESCRIPTION

In general, the present invention relates to various processes for the pyrolysis of carbohydrates to prepare products such as glycolaldehyde, methylglyoxal/pyruvaldehyde, acetol/hydroxyacetone, and formaldehyde. The present invention further relates to various catalysts and processes for preparing catalysts useful for carbohydrate pyrolysis. "Carbohydrate(s)" and/or "carbohydrate feed" as used herein will be understood as including biomass feedstocks in any form which contain or which provide carbohydrates, especially carbohydrates having four or more carbon atoms, from which glycolaldehyde may be obtained under pyrolytic conditions.

Various processes of the present invention have been found to produce glycolaldehyde in enhanced yields. Prior attempts to increase yields of glycolaldehyde have primarily focused on modifying feed concentrations and reactor conditions while the bed material and/or pyrolysis catalyst has remained largely unchanged. However, it has been surprisingly discovered that the pyrolysis catalyst (typically, though not necessarily, in the form of a fluidizable, supported catalyst combined with the conventional bed material or materials supplied for heat transfer to the carbohydrate feed) can greatly affect the pyrolysis reaction and overcome the problems encountered by prior processes.

Among other things, as discussed herein, it has been discovered that certain metal oxides are particularly effective in improving the yield of desirable products such as glycolaldehyde from the pyrolysis of carbohydrates, especially sugars such as glucose. The pyrolysis processes described herein incorporating these catalysts can advantageously provide for improved process economics and reduced amounts of undesired products that may require separation from the product mixture and special handling and disposal. For example, the pyrolysis processes using these catalysts may make more productive use of process inputs (e.g., by requiring less energy), produce reduced amounts of undesired byproducts, and/or produce less char in producing a given quantity of glycolaldehyde and other desired products, than would be experienced in the absence of the catalysts. Further, various processes described herein have the advantage of providing for stable product yields over extended operation and/or at high reactor throughputs.

Accordingly, embodiments of the present invention relate to various improved pyrolysis processes for preparing glycolaldehyde. For example, various embodiments relate to processes for preparing glycolaldehyde comprising: feeding a feed composition comprising a carbohydrate having at least four carbon atoms to a pyrolysis reaction zone; and pyrolyzing the carbohydrate in the presence of water and a catalyst in the pyrolysis reaction zone to form a reaction product comprising glycolaldehyde, wherein the catalyst comprises a metal oxide on a catalyst support.

Feed Materials

As noted, the feed composition comprises a carbohydrate having at least four carbon atoms. For example, in some embodiments, the carbohydrate comprises a $C_4$-$C_{24}$ carbohydrate. Such carbohydrates can be obtained from various conventional biorenewable sources such as corn grain (maize), wheat, potato, cassava and rice, as well as alternative sources such as energy crops, plant biomass, agricultural wastes, forestry residues, sugar processing residues, and plant-derived household wastes. In various embodiments, the carbohydrate is obtained from a grain crop (e.g., corn, wheat, soybean, rice, barley, rye, millet, sorghum, etc.). More generally, biorenewable sources that can be used include any renewable organic matter that includes a source of carbohydrates such as, for example, switch grass, *miscanthus*, trees (hardwood and softwood), vegetation, and crop residues (e.g., bagasse and corn stover). Other sources include, for example, waste materials (e.g., spent paper, green waste, municipal waste, etc.). Carbohydrates can be isolated from biorenewable materials using known methods. The carbohydrates may be provided in the form of a carbohydrate solution (e.g., an aqueous glucose solution) or as comminuted solids of such biomasses.

Carbohydrates obtained from these sources can include various monosaccharides, disaccharides, oligosaccharides, and polysaccharides. For example, in some embodiments, the carbohydrate comprises a $C_4$-$C_{24}$ saccharide. In certain embodiments, the carbohydrate comprises at least one saccharide selected from the group consisting of a monosaccharide, a disaccharide, an oligosaccharide, and combinations thereof. In various embodiments, the carbohydrate comprises a monosaccharide. Carbohydrates can also include a cellulose.

In some embodiments, the carbohydrate includes a sugar having at least four carbon atoms. For example, sugars include various aldoses. Aldoses, as referred to herein, include various compounds possessing an aldehyde and hydroxyl groups, which can be represented by formula (I):

$$HOCH_2(HCOH)_w CHO \qquad (I)$$

where w can be, for example, an integer from 2 to 10 or, in some embodiments, from 2 to 5. In various embodiments, the carbohydrate comprises at least one $C_4$-$C_7$ aldose. In some embodiments, the carbohydrate comprises at least one sugar selected from the group consisting of tetrose, pentose, hexose, heptose, and mixtures thereof. Specific $C_4$-$C_7$ aldoses include, for example, threose, erythrose, xylose, ribose, arabinose, glucose, galactose, mannose, glucoheptose, L-glycero-D-manno-heptose, and mixtures thereof. In various embodiments, the carbohydrate comprises a hexose such as glucose (dextrose). In some embodiments, the carbohydrate comprises a pentose such as xylose, ribose, and/or arabinose. The term "aldoses" and any specific aldose mentioned herein and as defined by formula (I) also include cyclic forms (hemiacetal forms) of these compounds.

In some embodiments, the carbohydrate includes a ketose sugar having at least four carbon atoms. In various embodiments, the carbohydrate comprises at least one ketose sugar selected from the group consisting of a ketotetrose, ketopentose, ketohexose, ketoheptose, and mixtures thereof. In certain embodiments, the carbohydrate comprises fructose.

The feed composition can have a carbohydrate concentration that is about 1 wt. % or greater, about 5 wt. % or greater, about 10 wt. % or greater, about 15 wt. % or greater, or about 20 wt. % or greater. For example, in various embodiments, the feed composition has a carbohydrate concentration that is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

Pyrolysis Catalyst

As noted, the pyrolysis reaction in the processes described herein are conducted in the presence catalyst comprising a metal oxide on a catalyst support. In various embodiments, the metal oxide comprises a transition metal oxide. For example, the metal oxide comprises an oxide of a group 4, 5, 6, 7, 8, 9, 10, or 11 metal or a mixture thereof. In some embodiments, the metal oxide comprises an oxide of a group 4, 5, or 6 metal or a mixture thereof. In certain embodiments, metal oxide comprises an oxide of titanium, molybdenum, tungsten, vanadium, or a mixture thereof. In particular embodiments, the metal oxide comprises an oxide of a molybdenum, tungsten, vanadium, or a mixture thereof. In certain embodiments, the metal oxide comprises an oxide of tungsten, molybdenum, or a mixture thereof. Preferred metal oxides typically include those that preferentially catalyze retro-aldol chemistry.

Oxides of molybdenum and tungsten have been found to be particularly effective for the pyrolysis catalysts. Accordingly, in various embodiments the metal oxide comprises tungsten oxide. For instance, the tungsten oxide can comprise tungsten (IV) oxide and/or tungsten (V) oxide. In some embodiments, the metal oxide comprises molybdenum oxide.

In some embodiments, tungsten oxide and/or molybdenum oxide constitute a significant portion of the metal oxide on the catalyst support. For example, in some embodiments, tungsten oxide and/or molybdenum oxide constitutes about 1 wt. % or greater, about 2 wt. % or greater, about 3 wt. % or greater, about 4 wt. % or greater, about 5 wt. % or greater, about 10 wt. % or greater, about 15 wt. % or greater, about 20 wt. % or greater, about 25 wt. % or greater, about 30 wt. % or greater, about 35 wt. % or greater, about 40 wt. % or greater, about 45 wt. % or greater, about 50 wt. % or greater, about 60 wt. % or greater, about 70 wt. % or greater, about 80 wt. % or greater, about 90 wt. % or greater, about 95 wt. % or greater, or about 99 wt. % or greater of the metal oxide on the catalyst support. In various embodiments, tungsten oxide and/or molybdenum oxide constitutes from about 1 wt. % to about 99 wt. %, from about 2 wt. % to about 99 wt. %, from about 3 wt. % to about 99 wt. %, from about 4 wt. % to about 99 wt. %, from about 5 wt. % to about 99 wt. %, from about 10 wt. % to about 99 wt. %, from about 15 wt. % to about 99 wt. %, from about 20 wt. % to about 99 wt. %, from about 25 wt. % to about 99 wt. %, from about 30 wt. % to about 99 wt. %, from about 35 wt. % to about 99 wt. %, from about 40 wt. % to about 99 wt. %, from about 45 wt. % to about 99 wt. %, from about 50 wt. % to about 99 wt. %, from about 60 wt. % to about 99 wt. %, from about 70 wt. % to about 99 wt. %, from about 80 wt. % to about 99 wt. %, from about 90 wt. % to about 99 wt. %, from about 95 wt. % to about 99 wt. %, from about 1 wt. % to about 95 wt. %, from about 2 wt. % to about 95 wt. %, from about 3 wt. % to about 95 wt. %, from about 4 wt. % to about 95 wt. %, from about 5 wt. % to about 95 wt. %, from about 10 wt. % to about 95 wt. %, from about 15 wt. % to about 95 wt. %, from about 20 wt. % to about 95 wt. %, from about 25 wt. % to about 95 wt. %, from about 30 wt. % to about 95 wt. %, from about 35 wt. % to about 95 wt. %, from about 40 wt. % to about 95 wt. %, from about 45 wt. % to about 95 wt. %, from about 50 wt. % to about 95 wt. %, from about 60 wt. % to about 95 wt. %, from about 70 wt. % to about 95 wt. %, from about 80 wt. % to about 95 wt. %, from about 90 wt. % to about 95 wt. %, from about 1 wt. % to about 90 wt. %, from about 2 wt. % to about 90 wt. %, from about 3 wt. % to about 90 wt. %, from about 4 wt. % to about 90 wt. %, from about 5 wt. % to about 90 wt. %, from about 10 wt. % to about 90 wt. %, from about 15 wt. % to about 90 wt. %, from about 20 wt. % to about 90 wt. %, from about 25 wt. % to about 90 wt. %, from about 30 wt. % to about 90 wt. %, from about 35 wt. % to about 90 wt. %, from about 40 wt. % to about 90 wt. %, from about 45 wt. % to about 90 wt. %, from about 50 wt. % to about 90 wt. %, from about 60 wt. % to about 90 wt. %, from about 70 wt. % to about 90 wt. %, or from about 80 wt. % to about 90 wt. % of the metal oxide on the catalyst support. In certain embodiments, the metal oxide on the catalyst support consists of tungsten oxide and/or molybdenum oxide.

The catalyst can have a metal oxide loading of about 0.1 wt. % or greater, about 0.5 wt. % or greater, about 1 wt. % or greater, about 2 wt. % or greater, about 5 wt. % or greater, about 10 wt. % or greater, about 20 wt. % or greater, about 30 wt. % or greater, about 40 wt. % or greater, about 50 wt. % or greater, about 60 wt. % or greater, about 70 wt. % or greater, about 80 wt. % or greater, about 90 wt. % or greater, about 95 wt. % or greater, or about 99 wt. % or greater. For example, in various embodiments, the catalyst has a metal oxide loading of from about 0.1 wt. % to about 15 wt. %, from about 0.5 wt. % to about 15 wt. %, from about 1 wt. % to about 15 wt. %, from about 2 wt. % to about 15 wt. %, from about 5 wt. % to about 15 wt. %, from about 0.1 wt. % to about 10 wt. %, from about 0.5 wt. % to about 10 wt. %, from about 1 wt. % to about 10 wt. %, from about 2 wt. % to about 10 wt. %, or from about 5 wt. % to about 10 wt. %.

In some cases, it has been found that low surface area catalysts and catalyst supports provide for greater product yields (e.g., greater yields of glycolaldehyde). Accordingly, in some embodiments, the catalyst support comprises a material that has a relatively low surface area (e.g., a BET specific surface area of about 500 $m^2/g$ or less, about 250 $m^2/g$ or less, about 100 $m^2/g$ or less, about 50 $m^2/g$ or less, about 25 $m^2/g$ or less, about 10 $m^2/g$ or less, about 5 $m^2/g$ or less, or about 1 $m^2/g$ or less).

In various embodiments, the catalyst support comprises a material selected from the group consisting of glass, ceramic, refractory material, and mixtures thereof. In some embodiments, the catalyst support comprises a glass material. In certain embodiments, the glass material comprises glass beads (e.g., glass spheres or similar geometric or amorphous shapes). In some embodiments, the catalyst support comprises a ceramic material selected from the group consisting of silicon carbide, yttria-stabilized zirconia, and combinations thereof. In certain embodiments, the catalyst support comprises a material that is substantially nonporous and has a relatively low surface area.

The catalysts described herein can provide for an extended time on stream (TOS) period. In some embodiments, the TOS of the catalyst is about 1,500 hours or greater, about 2,000 hours or greater, about 4,000 hours or greater, about 6,000 hours or greater, about 8,000 hours or greater, or about 10,000 hours or greater.

The catalyst can be prepared according to processes as described further herein. In some embodiments, the catalyst comprises a glass material and a coating comprising the metal oxide and the coating is deposited on the glass material coated using a sol-gel comprising the metal oxide or reaction product thereof. In these and other embodiments, the catalyst is an uncalcined catalyst.

Pyrolysis Process Features

As noted, pyrolysis is an energy intensive process requiring elevated temperatures in the pyrolysis reaction zone. In various embodiments, the pyrolysis reaction zone is heated to a temperature of about 400° C. or greater, about 450° C. or greater, about 475° C. or greater, about 500° C. or greater, about 525° C. or greater, about 550° C. or greater, about 575° C. or greater, or about 600° C. or greater. In some embodiments, the pyrolysis reaction zone is heated to a temperature of from about 400° C. to about 600° C., from about 400° C. to about 575° C., from about 400° C. to about 550° C., from about 400° C. to about 525° C., from about 450° C. to about 600° C., from about 450° C. to about 575° C., from about 450° C. to about 550° C., from about 450° C. to about 525° C., from about 500° C. to about 600° C., from about 500° C. to about 575° C., from about 500° C. to about 550° C., from about 500° C. to about 525° C., from about 525° C. to about 600° C., from about 525° C. to about 575° C., or from about 525° C. and about 550° C.

In addition to the pyrolysis catalyst comprising a metal oxide on a catalyst support, the pyrolysis reaction zone can further comprise a reaction zone media that is different than the catalyst. In various embodiments, the reaction zone media can include any inert material with which the catalyst can be combined and fluidized to provide a generally homogeneously distributed fluidized bed through which a carbohydrate feed composition and pyrolysis products may be carried as they are formed by an inert carrier gas, and which can be used to convey the thermal energy necessary to pyrolyze the carbohydrates in the carbohydrate feed and convert the carbohydrate(s) to pyrolysis products inclusive at least of glycolaldehyde. Those of skill in the art will be well able to identify a variety of materials that would be able to perform these essential functions. In various embodiments, the reaction zone media comprises a material selected from the group consisting of glass, ceramic, refractory material, and mixtures thereof. In some embodiments, the reaction zone media comprises a glass material. In some embodiments, the reaction zone media comprises a ceramic material selected from the group consisting of silicon carbide, yttria-stabilized zirconia, and combinations thereof. In certain embodiments, the glass material comprises glass beads (e.g., glass spheres or similar geometric or amorphous shapes) and/or sand.

As noted, the reaction zone media is typically different than the catalyst comprising a metal oxide on a support. Accordingly, in various embodiments, the reaction zone media is uncoated. In certain embodiments, the reaction zone media is free or essentially free (e.g., less than 1 wt. % or even less than 0.1 wt. %) of a metal oxide coating. In some embodiments, the reaction zone media comprises the support of the catalyst without metal oxide (i.e., the bare catalyst support).

The catalyst and reaction zone media can constitute a total volume of media loaded within the pyrolysis reaction zone, such that the catalyst is from about 1 vol. % to about 50 vol. %, from about 2 vol. % to about 25 vol. %, from about 3 vol. % to about 15 vol. %, or from about 4 vol. % to about 10 vol. % of the total volume of media loaded within the pyrolysis reaction zone.

In various embodiments, the feed composition is fluidized in a fluidizing or carrier gas in the pyrolysis reaction zone. Fluidizing gases include, for example, various inert gases or inert gas mixtures. In some embodiments, the fluidizing gas comprises nitrogen, steam, carbon dioxide, and/or waste gases such as combustion off-gas. In some embodiments, e.g., wherein the carbohydrate is provided in the form of a carbohydrate solution, the process further comprises atomizing the feed composition fed to the pyrolysis reaction zone. In certain embodiments, the feed composition can be atomized using a fluidizing gas (e.g., nitrogen, steam, etc.).

The average residence time of the carbohydrate feed in the pyrolysis reaction zone can be relatively fast. For example, in some embodiments the residence time is about 10 seconds or less, about 8 seconds or less, about 6 seconds or less, about 4 seconds or less, about 2 seconds or less, about 1 second or less, or about 0.5 seconds or less. In certain embodiments, the residence time is from about 0.5 seconds to about 10, from about 0.5 seconds to about 5 seconds, from about 0.5 seconds to about 2 seconds, from about 0.5 seconds to about 1 second, from about 1 second to about 10, from about 1 second to about 5 seconds, or from about 1 second to about 2 seconds.

In general, the reaction zone can include one or more batch, semi-batch, or continuous reactor designs using fixed bed reactors, trickle bed reactors, slurry phase reactors, moving bed reactors, or any other design that allows for catalytic reactions, particularly heterogeneous catalytic reactions. Examples of reactors can be seen in *Chemical Process Equipment—Selection and Design*, Couper et al., Elsevier 1990, which is incorporated herein by reference. In various processes described herein, the pyrolysis reaction zone comprises one or more fluidized bed reactors. It should be understood that feed compositions, any fluidizing gas, and catalysts can be introduced into a suitable reactor separately or in various combinations.

Various processes of the present invention have been found to provide for enhanced product yields. For example, various processes described herein, as demonstrated herein using a 20 wt. % aqueous glucose solution as the carbohydrate feed, provide a yield of glycolaldehyde that is about 70% or greater, about 75% or greater, or about 80% or greater. In some embodiments, the yield of glycolaldehyde is from about 70% to about 85%, from about 70% to about 80%, from about 75% to about 85%, or from about 75% to about 80%.

The reaction product can further comprise other minor components. In various embodiments, the reaction product comprises at least one other component selected from the group consisting of formaldehyde, glyoxal, pyruvaldehyde, acetol, and mixtures thereof. In some embodiments, the reaction product further comprises formaldehyde. In certain embodiments, the reaction product further comprises formaldehyde and the molar ratio of glycolaldehyde to formaldehyde is about 5:1 or greater, about 6:1 or greater, about 8:1 or greater, about 10:1 or greater, or about 12:1 or greater.

In various embodiments, the reaction product further comprises glyoxal. In some embodiments, the reaction product further comprises glyoxal and the molar ratio of glycolaldehyde to glyoxal is about 10:1 or greater, about 15:1 or greater, about 20:1 or greater, or about 25:1 or greater.

In various embodiments, the reaction product further comprises pyruvaldehyde. In some embodiments, the reaction product further comprises pyruvaldehyde and the molar ratio of glycolaldehyde to pyruvaldehyde is about 5:1 or greater, about 6:1 or greater, about 8:1 or greater, about 10:1 or greater, or about 12:1 or greater.

In various embodiments, the reaction product further comprises acetol. In some embodiments, the reaction product further comprises acetol and the molar ratio of glycolaldehyde to acetol is about 15:1 or greater, about 20:1 or greater, about 25:1 or greater, or about 30:1 or greater.

In various embodiments, the reaction product is free or essentially free of ethylene glycol. In some embodiments, the molar ratio of glycolaldehyde to ethylene glycol is about 100:1 or greater; about 200:1 or greater; or about 400:1 or greater.

The processes of the present invention can include various combinations of features as described herein. For example, various processes for preparing glycolaldehyde can comprise:

feeding a feed composition comprising a carbohydrate having at least four carbon atoms to a pyrolysis reaction zone; and pyrolyzing the carbohydrate in the presence of water and a catalyst in the pyrolysis reaction zone to form a reaction product comprising glycolaldehyde, wherein the catalyst comprises a metal oxide on a catalyst support and at least one of the following conditions is satisfied:

(a) the pyrolysis reaction zone is heated to a temperature of about 400° C. or greater;

(b) the catalyst support has a BET specific surface area that is about 500 $m^2/g$ or less, about 250 $m^2/g$ or less, about 100 $m^2/g$ or less, about 50 $m^2/g$ or less, about 25 $m^2/g$ or less, about 10 $m^2/g$ or less, about 5 $m^2/g$ or less, or about 1 $m^2/g$ or less;

(c) the catalyst support comprises a glass material;

(d) the pyrolysis reaction zone further comprises a reaction zone media that is different than the catalyst; and/or (e) the yield of glycolaldehyde is about 70% or greater, about 75% or greater, or about 80% or greater.

Catalyst Preparation

The pyrolysis catalyst can be prepared by various techniques. The metal oxide can be deposited on the catalyst supports using procedures including, but not limited to sol-gel, incipient wetness, ion-exchange, deposition-precipitation, and vacuum impregnation techniques.

In accordance with aspects of the present invention, one process for preparing a catalyst that has been found to be particularly effective comprises:

mixing a metal oxide, a solvent, and a strong acid to form a sol-gel;

depositing the sol-gel on a catalyst support to form a coated catalyst support; and removing solvent from the coated catalyst support to form the catalyst.

In some embodiments, the sol-gel is prepared by mixing a metal oxide, a peroxide source and a solvent. In further embodiments, the peroxide source comprises hydrogen peroxide and the solvent comprises water.

The metal oxide, metal oxide loading, and support can be any of those as specified herein for the pyrolysis catalyst. For example, in some embodiments, the metal oxide can comprise tungsten oxide and/or molybdenum oxide and the support can comprise a low surface area material such as glass (e.g., glass beads).

In various embodiments, the solvent comprises a $C_1$-$C_{10}$ alkanol. For example, the $C_1$-$C_{10}$ alkanol is selected from the group consisting of isopropanol, ethanol, and mixtures thereof. Further, the strong acid can be selected from the group consisting of hydrochloric acid, sulfuric acid, nitric acid, and mixtures thereof.

The sol-gel may be formed in air or it may be formed in an inert atmosphere. In some embodiments, the sol-gel is formed in an inert atmosphere. For example, the sol-gel can be formed in a nitrogen atmosphere. Further, the sol-gel can be formed in the substantial absence of oxygen. In various embodiments the sol-gel can be prepared by mixing a metal oxide, a peroxide source and a solvent. In some embodiments the peroxide source may be hydrogen peroxide and the solvent may be water.

During solvent removal, the coated catalyst support can be heated to a temperature sufficient to vaporize any solvent on the coated catalyst. In various embodiments, the coated catalyst support is heated to a temperature of about 80° C. or greater, about 90° C. or greater, or about 100° C. or greater to remove solvent. However, in various embodiments, the catalyst is not subjected to temperatures typical of calcination (e.g., about 500° C. or greater, about 750° C. or greater, or about 1000° C. or greater).

Having described the invention in detail, it will be apparent that modifications and variations are possible without departing from the scope of the invention defined in the appended claims.

EXAMPLES

The following non-limiting examples are provided to further illustrate the present invention.

Example 1: Preparing a Metal Oxide-Coated Glass Bead Catalyst

To prepare a metal oxide-coated glass bead catalyst, a metal oxide sol-gel was first prepared in a nitrogen-filled environment to prevent exposure to oxygen. 0.70 mL of a tungsten (V) ethoxide, 1,2-dimethoxyethane adduct, 99%, was added to 50 mL of isopropanol, while stirring. 0.2 mL of 2 M hydrochloric acid was then added in a dropwise manner, resulting in a pale-yellow sol containing a white precipitate. The mixture was stirred at room temperature for approximately one hour and allowed to rest overnight.

Glass beads were prepared by fuming the beads with isopropanol. 25 ml of the fumed beads were then added to the sol. The mixture containing the beads was mixed periodically and left uncovered. The resulting coated glass beads were evenly coated with the tungsten oxide solution.

The coated glass beads were then dried at ambient temperature and subjected to heat of approximately 80° C. overnight. The coated glass beads were not subjected to calcination or otherwise modified.

Each coated glass bead comprised approximately 0.25 wt. % tungsten in the form of a thin-film coating.

Example 2: Preparing a Metal Oxide-Coated Glass Bead Catalyst

An experiment following the procedure of Example 1 was performed, except that the coated glass beads were rinsed in acetone prior to heating at approximately 80° C. overnight. Rinsing the coated glass beads with acetone did not remove any meaningful amount of the tungsten oxide solution.

Example 3: Pyrolysis of Dextrose Utilizing a Glass Bead Catalyst

Untreated glass bead catalysts were tested for pyrolysis of dextrose utilizing a fluidized bed reactor system. The glass bead catalysts represented 6% of the total media volume of the reactor bed. An approximately 20 wt. % dextrose solution was introduced into the reactor system at a rate of 1.7 mL/min. A nitrogen gas stream was also directed into the system at a rate of 4500-5000 mL/min. Tables 1-3, below, report the product profile at various time on stream for differing reaction temperatures. Each of the reactions set forth below had a 0.98 s residence time.

TABLE 1

| | | | | | | | | |
|---|---|---|---|---|---|---|---|---|
| Reaction at 525° C. | | | | | | | | |
| Run | Time on Stream (hours) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
| R40-22-24 | 24 | 72.974 | 3.917 | 1.928 | 8.490 | 7.397 | — | — |
| R40-22-27 | 27 | 72.313 | 3.592 | 2.633 | 7.889 | 4.217 | 1.240 | 1.335 |
| R40-22-44 | 44 | 72.128 | 4.667 | 2.283 | 7.684 | 5.125 | — | — |

TABLE 2

Reaction at 550° C.

| Run | Time on Stream (hours) | Glucose (wt. %) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|---|
| R59-22-19 | 19 | 0.23 | 70.49 | 8.88 | 2.69 | 7.98 | 3.13 | 1.19 | 3.55 |
| R59-22-20 | 20 | 0.08 | 69.94 | 8.68 | 2.79 | 7.67 | 2.56 | 1.5  | 3.25 |
| R59-22-22 | 22 | 0    | 70.62 | 9.07 | 2.73 | 8.06 | 2.89 | 1.93 | 3.91 |
| R59-22-24 | 24 | 0    | 67.22 | 9.54 | 2.89 | 7.73 | 3.31 | 1.78 | 4.05 |
| R59-22-25 | 25 | 0.04 | 69.81 | 8.41 | 2.9  | 7.63 | 2.8  | 1.48 | 3.57 |
| R59-22-43 | 43 | 0    | 71.21 | 7.59 | 2.74 | 7.91 | 2.87 | 1.17 | 3.04 |
| R59-22-47 | 47 | 0.16 | 72.01 | 8.63 | 3.02 | 8.19 | 3.5  | 1.64 | 2.28 |
| R59-22-48 | 48 | 0    | 71.79 | 8.6  | 2.99 | 7.53 | 3.66 | 1.31 | 3.14 |

TABLE 3

Reaction at 550° C.

| Run | Time on Stream (hours) | Glucose (wt. %) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|---|
| R61-22-4  | 4  | 0   | 67.68 | 8.94 | 2.42 | 8.19 | 3.53 | —    | —     |
| R61-22-26 | 26 | 0   | 67.92 | 8.04 | 2.38 | 7.55 | 3.21 | 2.31 | 6.21  |
| R61-22-29 | 29 | 0.2 | 68.71 | 8.73 | 2.37 | 7.94 | 3.41 | 2.3  | 6.69  |
| R61-22-96 | 96 | 0   | 22.44 | 9.41 | 1.13 | 7.87 | 2.71 | 4.15 | 10.32 |

Example 4: Pyrolysis of Dextrose Utilizing Tungsten Carbide

A tungsten carbide grit material was mixed with glass beads and utilized in a fluidized bed reactor system for the pyrolysis or cracking of dextrose. The mixture was tested at varying reactor temperatures and compared to the experiment run with uncoated glass beads.

An approximately 20 wt. % dextrose solution was introduced into the reactor system at a rate of 1.7 mL/min. A nitrogen gas stream was also directed into the system at a rate of 4500-5000 mL/min. Tables 4 and 5 report the temperature at various points in the reactor system, flow rates, residence time, etc. The "Bottom Temperature" reported below is the temperature at the feed nozzle of the fluidized bed reactor. Table 6 reports the product profile for a given time on stream.

TABLE 4

| Run | Time On Stream (hours) | Set Temp. (° C.) | Top Temp. (° C.) | Upper Middle Temp. (° C.) | Middle Temp. (° C.) | Bottom Temp. (° C.) | Liquid Feed Flow Rate (ml/min) | N₂ Flow Rate Nozzle (ml/min) | N₂ Flow Rate Reactor (ml/min) |
|---|---|---|---|---|---|---|---|---|---|
| R50-22-1  | 1  | 500.0 | 546.7 | 571.8 | 549.4 | 1140.0 | 1.7 | 4493.4 | 0.0    |
| R50-22-3  | 3  | 500.0 | 523.3 | 525.5 | 612.4 | 1140.0 | 1.7 | 4992.6 | 0.0    |
| R50-22-7  | 7  | 475.0 | 499.9 | 506.5 | 585.0 | 1140.0 | 1.7 | 4992.8 | 1598.4 |
| R50-22-23 | 23 | 475.0 | 500.9 | 510.0 | 581.1 | 1140.0 | 1.7 | 4993.4 | 1598.9 |
| R50-22-27 | 27 | 475.0 | 501.7 | 519.0 | 575.5 | 1140.0 | 2.0 | 4992.2 | 1598.9 |
| R50-22-29 | 29 | 460.0 | 484.9 | 501.5 | 556.5 | 1140.0 | 1.7 | 4992.0 | 1599.0 |

TABLE 5

| Run | Time On Stream (hours) | Residence Time (s) | Mass Collected (g) | % Recovery |
|---|---|---|---|---|
| R50-22-1  | 1  | 1.044 | 15.814 | 92.37 |
| R50-22-3  | 3  | 0.967 | 16.011 | 93.52 |
| R50-22-7  | 7  | 0.809 | 15.871 | 92.70 |
| R50-22-23 | 23 | 0.809 | 16.039 | 93.9  |
| R50-22-27 | 27 | 0.772 | 20.502 | 97.43 |
| R50-22-29 | 29 | 0.825 | 16.029 | 93.63 |

TABLE 6

| Run | Time On Stream (hours) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|
| R50-22-1 | 1 | 51.98 | 8.22 | 2.19 | 6.82 | 2.65 | 6.58 | 4.86 |
| R50-22-3 | 3 | 51.36 | 8.41 | 3.28 | 7.10 | 2.19 | 6.31 | 3.78 |
| R50-22-7 | 7 | 60.95 | 9.89 | 2.48 | 7.61 | 1.70 | 3.20 | 2.09 |
| R50-22-23 | 23 | 63.81 | 8.87 | 2.30 | 7.55 | 1.62 | 2.08 | 2.32 |
| R50-22-27 | 27 | 67.08 | 10.23 | 2.18 | 7.81 | 1.63 | 1.87 | 1.92 |
| R50-22-29 | 29 | 63.53 | 8.73 | 1.89 | 7.69 | 1.57 | 2.31 | 1.66 |

A second experiment utilizing tungsten carbide grit material mixed with glass beads was conducted under the same conditions. The cracking media comprised approximately 3% tungsten carbide grit and 97% glass beads, on a volume basis. Tables 7 and 8 report the temperature at various points in the reactor system, flow rates, residence time, etc. The product profile of this second experiment is reported below in Table 9.

TABLE 7

| Run | Time On Stream (hours) | Set Temp. (° C.) | Liquid Feed Flow Rate (ml/min) | $N_2$ Flow Rate Nozzle (ml/min) | $N_2$ Flow Rate Reactor (ml/min) |
|---|---|---|---|---|---|
| R51-22-3 | 3 | 525.0 | 1.7 | 4993.2 | −44.4 |
| R51-22-6 | 6 | 475.0 | 2.1 | 4992.6 | 1598.6 |
| R51-22-23 | 23 | 475.0 | 2.1 | 4993.0 | 1599.2 |
| R51-22-26 | 26 | 475.0 | 2.1 | 4992.7 | 1598.8 |

TABLE 8

| Run | Time On Stream (hours) | Residence Time (s) | Mass Collected (g) | % Recovery |
|---|---|---|---|---|
| R51-22-3 | 3 | 0.938 | 16.179 | 94.50 |
| R51-22-6 | 6 | 0.770 | 19.906 | 93.02 |
| R51-22-23 | 23 | 0.770 | 19.830 | 92.66 |
| R51-22-26 | 26 | 0.770 | 19.933 | 93.15 |

TABLE 9

| Run | Time On Stream (hours) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|
| R51-22-3 | 3 | 63.28 | 8.73 | 2.34 | 8.48 | 3.10 | 2.21 | 4.25 |
| R51-22-6 | 6 | 65.13 | 8.37 | 1.54 | 11.06 | 2.96 | 1.57 | 1.68 |
| R51-22-23 | 23 | 66.05 | 9.88 | 1.65 | 10.47 | 2.79 | 0.72 | 1.07 |
| R51-22-26 | 26 | 66.07 | 8.01 | 1.57 | 10.19 | 2.87 | 1.05 | 1.62 |

Example 5: Pyrolysis of Dextrose Utilizing a Tungsten Oxide-Coated Glass Bead Catalyst Several experiments similar to those conducted in Example 4 were performed. Tables 10 and 11 report the results using tungsten oxide coated glass bead catalysts at varying temperatures of the reactor system, wherein the tungsten oxide-coated catalysts represented approximately 6 wt. % of the total cracking media.

TABLE 10

Tungsten Oxide Catalyst

| Run | Time on Stream (hours) | Temp. (° C.) | Glucose (wt. %) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|---|---|
| R62-22-1 | 1 | 550 | 0 | 59.54 | 9.22 | 3 | 8.65 | 3.38 | 0 | 0 |
| R62-22-2 | 2 | 550 | 0.08 | 66.21 | 8.18 | 3.19 | 8.63 | 2.78 | 1.62 | 6.45 |
| R62-22-20 | 20 | 550 | 0 | 75.21 | 8.33 | 3.15 | 8.26 | 2.95 | 1.57 | 4.78 |
| R62-22-23 | 23 | 550 | 0.09 | 76.95 | 8.05 | 3.04 | 7.93 | 2.72 | 1.17 | 4.06 |
| R62-22-43 | 43 | 525 | 0 | 76.6 | 5.99 | 3.07 | 7.54 | 2.4 | 0.63 | 3.48 |
| R62-22-46 | 46 | 525 | 0.16 | 81.78 | 7.38 | 3.6 | 8.64 | 2.22 | 0.71 | 3.74 |
| R62-22-62 | 62 | 525 | 0.17 | 80.89 | 7.06 | 3.25 | 7.89 | 2.32 | 0 | 0 |

TABLE 11

Tungsten Oxide Catalyst

| Run | Time on Stream (hours) | Temp. (° C.) | Glucose (wt. %) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|---|---|
| R60-22-3 | 3 | 550 | 0.11 | 71.47 | 10.15 | 3.22 | 9.17 | 3.77 | 1.15 | 4.16 |
| R60-22-22 | 22 | 550 | 0 | 74.82 | 8.68 | 3.18 | 8.61 | 2.68 | 0.99 | 4.42 |
| R60-22-46 | 46 | 550 | 0 | 74.98 | 8.6 | 3.09 | 8.4 | 2.48 | 0.69 | 4.17 |
| R60-22-52 | 52 | 550 | 0 | 75.39 | 8.99 | 3.13 | 8.71 | 2.49 | 0.72 | 4.02 |
| R60-22-119 | 119 | 550 | 0 | 67.78 | 10.42 | 2.61 | 9.63 | 3.3 | 1.64 | 6 |
| R60-22-120 | 120 | 550 | 0.07 | 71.9 | 9.21 | 3.09 | 9.07 | 3.35 | 1.25 | 4.66 |
| R60-22-142 | 142 | 550 | 0 | 78.56 | 9.02 | 3.1 | 9.02 | 3.26 | 1.05 | 4.38 |
| R60-22-143 | 143 | 525 | 0 | 74.27 | 8.82 | 2.92 | 9.19 | 2.91 | 1.27 | 2.23 |
| R60-22-144 | 144 | 525 | 0.1 | 75.8 | 8 | 2.98 | 9.07 | 2.47 | 1.22 | 1.88 |
| R60-22-146 | 146 | 525 | 0 | 74.9 | 8.45 | 2.73 | 9.13 | 2.87 | 1.36 | 3.18 |
| R60-22-147 | 147 | 525 | 0 | 76.4 | 8.35 | 2.94 | 9.17 | 2.76 | 2.3 | 2.39 |
| R60-22-148 | 148 | 525 | 0.16 | 77.96 | 8.46 | 2.93 | 9.01 | 2.83 | 1.04 | 2.46 |
| R60-22-165 | 165 | 525 | 0.06 | 78.02 | 8.28 | 2.84 | 8.42 | 2.45 | 0.9 | 2.72 |
| R60-22-167 | 167 | 500 | 0 | 79.2 | 8.47 | 2.98 | 9.21 | 2.49 | 0.85 | 3.18 |
| R60-22-169 | 169 | 500 | 0 | 77.67 | 10.23 | 2.89 | 10.09 | 3.18 | 0.88 | 2.29 |

As demonstrated by the above results, a catalyst comprising metal oxide-coated glass beads produced a considerably higher yield of glycolaldehyde as compared to a metal carbide catalyst.

Example 6: Pyrolysis of Dextrose Utilizing a Molybdenum Oxide-Coated Glass Bead Catalyst A similar experiment to Example 4 was performed using a molybdenum oxide-coated glass bead catalyst that represented approximately 6 wt. % of the total cracking media. The catalyst was tested at varying reactor temperatures. The reaction conditions are set forth in Table 12 and the results are reported in Table 13.

TABLE 12

| Run | Time on Stream (hours) | $N_2$ Flow Rate (ml/min) | Feed Flow Rate (ml/min) | Temp. (° C.) | Residence Time (Sec) | Mass Collected (g) | % Recovery |
|---|---|---|---|---|---|---|---|
| R70-22-2 | 2 | 4673.46 | 1.65 | 525 | 0.981 | 16.2205 | 94.75 |
| R70-22-5 | 5 | 4672.95 | 1.65 | 525 | 0.981 | 16.4251 | 95.94 |
| R70-22-23 | 23 | 4673.36 | 1.65 | 525 | 0.981 | 16.5128 | 96.45 |
| R70-22-30 | 30 | 4653.02 | 1.65 | 525 | 0.984 | 16.7143 | 97.63 |
| R70-22-47 | 47 | 4722.83 | 1.65 | 525 | 0.973 | 16.7549 | 97.87 |
| R70-22-53 | 53 | 4852.57 | 1.65 | 525 | 0.986 | 16.7271 | 97.71 |
| R70-22-122 | 122 | 4652.67 | 1.65 | 525 | 0.984 | 16.8052 | 98.16 |
| R70-22-144 | 144 | 4652.33 | 1.65 | 525 | 0.986 | 16.9679 | 99.11 |
| R70-22-169 | 169 | 4652.48 | 1.65 | 525 | 0.985 | 17.1050 | 99.91 |
| R70-22-193 | 193 | 4652.84 | 1.65 | 525 | 0.985 | 16.9095 | 98.77 |
| R70-22-197 | 197 | 4652.77 | 1.65 | 525 | 0.985 | 16.6974 | 97.53 |

TABLE 12-continued

| Run | Time on Stream (hours) | N₂ Flow Rate (ml/min) | Feed Flow Rate (ml/min) | Temp. (° C.) | Residence Time (Sec) | Mass Collected (g) | % Recovery |
|---|---|---|---|---|---|---|---|
| R70-22-217 | 217 | 4653.05 | 1.65 | 525 | 0.983 | 16.6044 | 96.99 |
| R70-22-289 | 289 | 4652.82 | 1.65 | 525 | 0.985 | 16.7214 | 97.67 |
| R70-22-337 | 337 | 4652.69 | 1.65 | 525 | 0.985 | 16.8754 | 98.57 |
| R70-22-366 | 366 | 4652.81 | 1.65 | 525 | 0.984 | 16.8459 | 98.40 |
| R70-22-457 | 457 | 4652.75 | 1.65 | 525 | 0.985 | 16.6437 | 97.22 |
| R70-22-506 | 506 | 4652.87 | 1.65 | 525 | 0.981 | 16.2371 | 94.84 |
| R70-22-672 | 672 | 4652.32 | 1.65 | 525 | 0.985 | 16.3954 | 95.77 |

TABLE 13

| Run | Time on Stream (hours) | Temp. (° C.) | Glucose (wt. %) | Glycolaldehyde (wt. %) | Formaldehyde (wt. %) | Glyoxal (wt. %) | Pyruvaldehyde (wt. %) | Acetol (wt. %) |
|---|---|---|---|---|---|---|---|---|
| R70-22-2 | 2 | 525 | 0.05 | 66.01 | 9.43 | 4.54 | 9.42 | 2.30 |
| R70-22-5 | 5 | 525 | 0.06 | 73.79 | 8.27 | 4.45 | 9.17 | 1.81 |
| R70-22-23 | 23 | 525 | 0.15 | 76.99 | 7.42 | 4.26 | 8.68 | 1.51 |
| R70-22-30 | 30 | 525 | 0.12 | 79.36 | 8.13 | 4.27 | 9.15 | 1.66 |
| R70-22-47 | 47 | 525 | 0.13 | 78.66 | 8.21 | 4.25 | 9.09 | 1.61 |
| R70-22-53 | 53 | 525 | 0.15 | 79.83 | 7.65 | 3.61 | 8.68 | 1.20 |
| R70-22-122 | 122 | 525 | 0.07 | 79.86 | 7.87 | 4.12 | 9.03 | 1.58 |
| R70-22-144 | 144 | 525 | 0.00 | 79.76 | 7.74 | 4.34 | 8.74 | 1.56 |
| R70-22-169 | 169 | 525 | 0.06 | 80.01 | 7.33 | 3.96 | 8.53 | 1.63 |
| R70-22-193 | 193 | 525 | 0.10 | 80.11 | 7.29 | 4.01 | 8.51 | 1.53 |
| R70-22-197 | 197 | 525 | 0.00 | 78.45 | 8.85 | 4.60 | 10.02 | 1.54 |
| R70-22-217 | 217 | 525 | 0.06 | 81.19 | 8.11 | 4.15 | 9.28 | 1.58 |
| R70-22-289 | 289 | 525 | 0.06 | 80.14 | 5.99 | 3.31 | 8.13 | 1.49 |
| R70-22-337 | 337 | 525 | 0.00 | 82.40 | 8.44 | 4.20 | 9.48 | 1.48 |
| R70-22-366 | 366 | 525 | 0.07 | 82.31 | 8.30 | 3.92 | 9.53 | 1.56 |
| R70-22-457 | 457 | 525 | 0.12 | 83.69 | 7.92 | 3.92 | 9.75 | 1.46 |
| R70-22-506 | 506 | 525 | 0.00 | 85.27 | 8.51 | 4.05 | 9.87 | 1.66 |
| R70-22-672 | 672 | 525 | 0.05 | 66.01 | 9.43 | 4.54 | 9.42 | 2.30 |

Example 7: Pyrolysis of Dextrose Utilizing a Vanadium Oxide-Coated Glass Bead Catalyst A similar experiment to Example 4 was performed using a 5 wt. % vanadium oxide-coated glass bead catalyst. This catalyst was used in a reaction with a set temperature 525° C. After about 50 hours on stream, coking of the reactor was observed.

The reaction conditions are set forth below in Table 14. Table 15 reports the temperature at various points in the reactor during the reaction. The "Bottom Temperature" below is the temperature at the feed nozzle. Table 16 reports the product profile of the reaction product.

TABLE 14

| Run | Time On Stream (hours) | N₂ Flow Rate (ml/min) | Water Flow Rate (ml/min) | Feed Flow Rate (ml/min) | Water Vapor Flow Rate (ml/min) | Residence Time (s) | Mass Collected (g) | % Recovery |
|---|---|---|---|---|---|---|---|---|
| R73-22-27 | 27 | 4652.79 | 0.00 | 1.65 | 0.00 | 0.99 | 16.37 | 95.64 |
| R73-22-50 | 50 | 4653.22 | 0.86 | 0.79 | 0.86 | 0.96 | 1.87 | 23.70 |

TABLE 15

| Run | Time On Stream (hours) | Top Temperature (° C.) | Upper Middle Temperature (° C.) | Middle Temperature (° C.) | Bottom Temperature (° C.) |
|---|---|---|---|---|---|
| R73-22-27 | 27 | 545.83 | 548.66 | 628.23 | 97.73 |
| R73-22-50 | 50 | 545.83 | 541.59 | 628.23 | 97.73 |

TABLE 16

| Run | Time on Stream (hours) | Glucose (wt. %) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|---|
| R73-22-27 | 27 | 0.11 | 68.70 | 9.39 | 3.43 | 9.30 | 2.90 | 1.41 | 4.78 |
| R73-22-50 | 50 | 0.00 | 15.92 | 2.99 | 0.62 | 2.47 | 0.82 | 3.81 | 10.40 |

Example 8: Pyrolysis of Dextrose Utilizing a Molybdenum-Coated Quartz Sand Catalyst A similar experiment to Example 4 was performed using a cracking media that was approximately 5 wt. % molybdenum-coated quartz sand catalyst and 95 wt. % untreated quartz sand. The reaction was conducted at a set temperature of 525° C. The reaction conditions are set forth below in Tables 17 and 18. The "Bottom Temperature" reported below is the temperature at the feed nozzle. Table 19 reports the results of the experiment.

After 3 hours on stream the reaction was stopped, and the reactor was inspected. Coking was observed and a solid mass had formed in the reactor.

TABLE 17

| Run | Time On Stream (hours) | N₂ Flow Rate (ml/min) | Feed Flow Rate (ml/min) | Residence Time (s) | Mass Collected (g) | % Recovery |
|---|---|---|---|---|---|---|
| R74-22-3 | 3 | 4992.48 | 1.60 | 0.94 | 13.46 | 81.18 |

TABLE 18

| Run | Time On Stream (hours) | Top Temperature (° C.) | Upper Middle Temperature (° C.) | Middle Temperature (° C.) | Bottom Temperature (° C.) |
|---|---|---|---|---|---|
| R74-22-3 | 3 | 535.69 | 536.08 | 593.37 | 73.45 |

TABLE 19

| Run | Time On Stream (hours) | Glucose (wt. %) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|---|
| R74-22-3 | 3 | 0.00 | 8.72 | 5.50 | 1.82 | 0.00 | 0.00 | 1.58 | 8.07 |

Example 9: Pyrolysis of Dextrose Utilizing a Titania-Coated Glass Bead Catalyst A titania oxide-coated glass bead was prepared in accordance with the procedure of Example 1 and an experiment for the pyrolysis of dextrose with this catalyst was tested in accordance with the procedure of Example 4. The reaction product profile is reported below in Table 20.

Prior to conducting the reaction, the entire reactor body and all gas handling lines were properly cleaned. The reactor failed to run for longer than 30 hours before completely sealing off. Upon investigation, a solid mass had formed in the reactor and the gas handling lines had become sealed with a mixture of char and pyrolysis oil. It was hypothesized that after injection, the feed reacted with the glass beads to form a solid mass and elevated amounts of char. This buildup ultimately caused the reactor to shut down to a pressure buildup.

TABLE 20

| Run | Time On Stream (hours) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|
| R71-22-22 | 22 | 71.35% | 8.36% | 8.36% | 9.43% | 1.97% | 1.48% | 3.67% |

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved, and other advantageous results attained.

As various changes could be made in the above processes and compositions without departing from the scope of the invention, it is intended that all matter contained in the above description shall be interpreted as illustrative and not in a limiting sense.

What is claimed is:

1. A process for preparing glycolaldehyde, the process comprising:
    feeding a feed composition comprising a carbohydrate having at least four carbon atoms to a pyrolysis reaction zone; and
    pyrolyzing the carbohydrate in the presence of water and a catalyst in the pyrolysis reaction zone to form a reaction product comprising glycolaldehyde, wherein the catalyst comprises a metal oxide on a catalyst support and at least one of the following conditions is satisfied:
    (a) the pyrolysis reaction zone is heated to a temperature of 400° C. or greater;
    (b) the catalyst support has a BET specific surface area that is 500 m$^2$/g or less, 250 m$^2$/g or less, 100 m$^2$/g or less, 50 m$^2$/g or less, 25 m$^2$/g or less, 10 m$^2$/g or less, 5 m$^2$/g or less, or 1 m$^2$/g or less;
    (c) the catalyst support comprises a glass, ceramic, or refractory material;
    (d) the pyrolysis reaction zone further comprises a reaction zone media that is different than the catalyst; and/or
    (e) the yield of glycolaldehyde is 70% or greater, 75% or greater, or 80% or greater.

2. The process of claim 1, wherein the carbohydrate comprises a C$_4$-C$_{24}$ carbohydrate.

3. The process of claim 1, wherein the carbohydrate comprises at least one C$_4$-C$_{24}$ saccharide selected from the group consisting of a monosaccharide, a disaccharide, an oligosaccharide, and combinations thereof.

4. The process of claim 1, wherein the carbohydrate comprises glucose (dextrose) and/or fructose.

5. The process of claim 1, wherein the feed composition comprises an aqueous solution comprising at least one of the carbohydrate or glucose.

6. The process of claim 1, wherein the metal oxide comprises a transition metal oxide.

7. The process of claim 1, wherein the metal oxide comprises an oxide of a group 4, 5, 6, 7, 8, 9, 10, or 11 metal or a mixture thereof.

8. The process of claim 1, wherein the metal oxide comprises an oxide of titanium, molybdenum, tungsten, vanadium, or a mixture thereof.

9. The process of claim 1, wherein the metal oxide comprises tungsten (IV) oxide, tungsten (V) oxide, or molybdenum oxide.

10. The process of claim 9, wherein tungsten oxide and/or molybdenum oxide constitutes 1 wt. % or greater, 2 wt. % or greater, 3 wt. % or greater, 4 wt. % or greater, 5 wt. % or greater, 10 wt. % or greater, 15 wt. % or greater, 20 wt. % or greater, 25 wt. % or greater, 30 wt. % or greater, 35 wt. % or greater, 40 wt. % or greater, 45 wt. % or greater, 50 wt. % or greater, 60 wt. % or greater, 70 wt. % or greater, 80 wt. % or greater, 90 wt. % or greater, 95 wt. % or greater, or 99 wt. % or greater of the metal oxide on the catalyst support.

11. The process of claim 1, wherein the catalyst has a tungsten and/or molybdenum oxide loading of 0.1 wt. % or greater, 0.5 wt. % or greater, 1 wt. % or greater, 2 wt. % or greater, 5 wt. % or greater, 10 wt. % or greater, 20 wt. % or greater, 30 wt. % or greater, 40 wt. % or greater, 50 wt. % or greater, 60 wt. % or greater, 70 wt. % or greater, 80 wt. % or greater, 90 wt. % or greater, 95 wt. % or greater, or 99 wt. % or greater.

12. The process of claim 1, wherein the catalyst has a tungsten and/or molybdenum metal oxide loading of from 0.1 wt. % to 15 wt. %, from 0.5 wt. % to 15 wt. %, from 1 wt. % to 15 wt. %, from 2 wt. % to 15 wt. %, from 5 wt. % to 15 wt. %, from 0.1 wt. % to 10 wt. %, from 0.5 wt. % to 10 wt. %, from 1 wt. % to 10 wt. %, from 2 wt. % to 10 wt. %, or from 5 wt. % to 10 wt. %.

13. The process of claim 1, wherein the catalyst support has a BET specific surface area that is 500 m$^2$/g or less, 250 m$^2$/g or less, 100 m$^2$/g or less, 50 m$^2$/g or less, 25 m$^2$/g or less, 10 m$^2$/g or less, 5 m$^2$/g or less, or 1 m$^2$/g or less.

14. The process of claim 1, wherein the catalyst support comprises a glass material, a ceramic material, refractory materials, and mixtures thereof.

15. The process of claim 1, wherein the ceramic material is selected from the group consisting of silicon carbide, yttria-stabilized zirconia, and combinations thereof.

16. The process of claim 14, wherein the refractory materials comprise silicon, aluminum, magnesium, calcium, zirconium, or combinations thereof.

17. The process of claim 1, wherein the catalyst is an uncalcined catalyst.

18. The process of claim 1, wherein the reaction zone media comprises a material selected from the group consisting of glass, ceramic, refractory material, and mixtures thereof.

19. The process of claim 1, wherein the reaction zone media is uncoated.

20. The process of claim 1, wherein the reaction zone media is free or essentially free of a metal oxide coating.

* * * * *